(12) United States Patent
Young

(10) Patent No.: US 7,192,730 B2
(45) Date of Patent: Mar. 20, 2007

(54) THERMOSTABLE PROTEOLYTIC ENZYMES AND USES THEREOF IN PEPTIDE AND PROTEIN SYNTHESIS

(75) Inventor: David Michael Young, Seal Cove, ME (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 404 days.

(21) Appl. No.: 10/825,921

(22) Filed: Apr. 15, 2004

(65) Prior Publication Data

US 2004/0229303 A1 Nov. 18, 2004

Related U.S. Application Data

(60) Continuation of application No. 10/379,952, filed on Mar. 4, 2003, now Pat. No. 6,743,618, which is a division of application No. 09/404,031, filed on Sep. 23, 1999, now Pat. No. 6,573,065, which is a division of application No. 09/197,945, filed on Nov. 23, 1998, now Pat. No. 6,143,517, which is a continuation of application No. 08/773,475, filed on Dec. 23, 1996, now abandoned.

(51) Int. Cl.
*C12Q 1/34* (2006.01)

(52) U.S. Cl. .................. 435/18; 435/23; 435/212; 435/219; 435/220

(58) Field of Classification Search .................. None
See application file for complete search history.

(56) References Cited

U.S. PATENT DOCUMENTS 5,242,817 A 9/1993 Kelly et al.
5,391,489 A 2/1995 Kelly et al.

OTHER PUBLICATIONS

Abrahmsen, L., et al. "Engineering subtilisin and its substrates for efficient ligation of peptide bonds in aqueous solution" *Biochemistry* (1991) 30:4151-4159.
Blumentals, I.I., et al. "Characterization of sodium dodecyl sulfate-resistant proteolytic activity in the hyperthermophilic Archaebacterium *Pyrococcus furiosus*" *Appl. and Environ. Microbiol.* (1990) 56(7):1992-1998.
Brennan, M.B. "Enzyme discovery heats up: enzymes that could maximize industrial processing reactions are reaped form exotic microorganisms" *C&EN* Oct. 1996:31-33.

Castellan, G.W. "Physical Chemistry", (2nd Edition), pp. 245-247; Addison-Wesley Publishing Comp., Reading, MA.
Chang, et al., "Protease I from *Pyrococcus furiosus*", *Methods in Enzymology* (2001), 330:403-413.
Christenen, U., et al. "Mechanism of carboxypeptidase-Y-catalyzed peptide symisynthesis" *Eur. J. Biochem.* (1992) 210:467-473.
De Vos, W.M., et al., "Purification, characterization, and molecular modelling of pyrolysin and other extracellular thermostable serine proteases from hyperthermophilic microorganisms", *Methods in Enzymology* (2001), 330:383-393.
Eggen, R., et al. "Characterization of pyrolysin, a hyperthermoactive serine protease from the Archaebacterium *Pyrococcus furiosus*" *FEMS Microbiol. Lett.* (1990) 71:17-20.
Fersht, A. "Enzyme Structure and Mechanism" 2nd Edition, W.H. Freeman and Company, New York, (1985) pp. 89-90.
Fiala, G. and Stetter, K.O. "*Pyrococcus furiosus s.* Nev. represents a novel genus of marine heterotrophic Archaebacteria growing optimally at 100°" *Arch Microbiol.* (1986) 145:56-61.
Halio, S.B., et al. "Sequence, expression in *Escherichia coli*, and analysis of the gene encoding a novel intracellular protease (Pfpl) from the hyperthermophilic Archaeon *Pyrococcus furiosus*" *J. Bacteriol.* (1996) 178(9):2605-2612.
Jencks W.P. "Catalysis in Chemistry and Enzymology" Dover Publication, Inc., New York, (1987) pp. 312-313.
Nakatsuka, T. et al., "Peptide segment coupling catalyzed by the semisynthetic enzyme thiolsubtilisin" *J. Am Chem. Soc.* (1987) 109:3808-3810.
Petkov, D.D. "Enzyme peptide synthesis and semisynthesis: kinetic and thermodynamic aspects" *J. Thero. Biol.* (1982) 98:419-425.
Stetter, K.O. "Microbial life in hyperthermal environments" *ASM News* (1995) 61(6):285-290.
Stetter, K.O., et al., "Hyperthermophilic microorganisms", *FEMS Microbiol. Rev.* (1990), 75:117-124.
Voohorst, W. et al. "Isolation and characterization of the hyperthermostable serine protease, pyrolysin, and its gene from the hyperthermophilic Archaeon *Pyrococcus furiosus*" *J. Biol. Chem.* (1996) 271(34):20426-20431.
Voorhorst, W.G.B., et al. "Homology modeling of two subtilisin-like serine proteases form the hyperthermophilic Archaea *Pyrococcus furiosus* and *Thermococcus stettem*" Protein Engineering (1997) 10(8):905-914.
Woese, C.R., et al., "Towards a natural system of organisms : proposal for the domans Archaea, Bacteria, and Eucarya", *Proc. Natl. Acad. Sci. USA* (1990) 87:4576-4579.

*Primary Examiner*—Nashaat T. Nashed
(74) *Attorney, Agent, or Firm*—Saliwanchik, Lloyd & Saliwanchik

(57) ABSTRACT

The subject invention pertains to new thermostable enzymes and the use of these enzymes both in proteolysis as well as protein and polypeptide synthesis. The subject invention further concerns polynucleotide sequences which encode the enzymes of the subject invention.

1 Claim, No Drawings

THERMOSTABLE PROTEOLYTIC ENZYMES AND USES THEREOF IN PEPTIDE AND PROTEIN SYNTHESIS

CROSS-REFERENCE TO A RELATED APPLICATION

The application is a continuation of U.S. Ser. No. 10/379,952, filed Mar. 4, 2003, now U.S. Pat. No. 6,743,618, which is a divisional of U.S. Ser. No. 09/404,031, filed Sep. 23, 1999, now U.S. Pat. No.6,573,065, which is a divisional of U.S. Ser. No. 09/197,945, filed Nov. 23, 1998, now U.S. Pat. No. 6,143,517, which is a continuation of U.S. Ser. No. 08/773,475 filed Dec. 23, 1996, now abandoned.

BACKGROUND OF THE INVENTION

Chemical reactions in biological systems are almost always facilitated by the action of one or more catalysts. Enzymes, which are proteins that catalyze biological reactions, are known for their catalytic efficiency and specificity. Enzymes typically accelerate reactions by factors of 1 million or more. Many reactions in biological systems do not occur at perceptible rates in the absence of enzymes.

Enzymes are highly specific in the type of reaction catalyzed as well as in the particular substrates which are acted upon. One broad category of enzymes includes the proteolytic enzymes which catalyze the hydrolysis of peptide bonds. Proteolytic enzymes, also known as proteases, vary significantly in their degree of specificity. For example, subtilisin, which comes from certain bacteria, will cleave peptide bonds regardless of the nature of the side chains adjacent to the bond. Trypsin is quite specific in that it splits peptide bonds on the carboxyl side of lysine and arginine residues only. Thrombin, an enzyme participating in blood clotting, is even more specific than trypsin. Thrombin only cleaves between arginine and glycine residues. These are only a very few examples of proteases; many other proteases are known. There are several general categories of proteases. These categories include serine, cysteine, aspartic, and metalloproteases. This classification is based on the most prominent functional group at the active site of the proteases. The serine proteases are of particular interest relative to the current invention.

Much information now exists on the molecular structure and function of many serine proteases from diverse species. The majority of these enzymes consist of a single polypeptide chain of molecular weight 25,000–30,000. Chymotrypsin and subtilisin are both members of the serine protease family. Like other proteases, serine proteases cleave peptide bonds within a polypeptide to produce two smaller peptides. The cleavage reaction will typically proceed through an intermediate transition state which is facilitated by the presence of the protease. For serine proteases, the formation of an acyl-enzyme intermediate involving a reactive serine residue is the first step in the hydrolysis reaction. Deacylation of the acyl-enzyme intermediate is the second step in the hydrolysis. Like other proteases, serine proteases achieve their catalytic activity by lowering the activation energy for a specific hydrolysis reaction.

Proteases can be obtained from a wide variety of sources including fungi, bacteria, and eukaryotic cells. Although proteases have been obtained from many bacteria, relatively few proteases have been identified from bacteria which are known to live in extremely hot environments. Bacteria capable of growing at or above 80° C.–100° C. are generally known as extreme thermophiles or hyperthermophiles. Such highly thermophilic microorganisms have been the object of considerable scrutiny by researchers attempting to gain insight into the biochemical mechanism which enables these microbes to survive under such extreme conditions.

A number of microorganisms have been isolated from extremely hot environments. These microorganisms have been studied and certain useful compounds have been identified. For example, thermostable DNA polymerases have been obtained from *Thermus aquaticus*. Proteases have been isolated from thermophiles including *T. aquaticus, Desulfurococcus* species, *Pyrococcus furiosus, Sulfolobus acidocaldarius, Thermococcus stetteri*, and *Pyrobaculum aerophilum*. However, difficulties in culturing extremophiles have limited the number of these microbes which have been characterized as well as the number of useful compounds isolated therefrom (Brennan, *Chemical and Engineering News*, Oct. 14, 1996).

Stetter, et al. identified microorganisms from the hot springs of Vulcano Island, Italy, that flourish at temperatures exceeding 100° C. (Stetter, K. O. "Microbial Life in Hyperthermal Environments," *ASM News* 61:285–290, 1995; Stetter, K. O., Fiala, G., Huber, R. And Segerer, A. "Hyperthermophilic Microorganisms," FEMS *Microbiol. Rev.* 75:117–124, 1990). While thermophilic organisms that grow optimally at 60° C. have been known for many years, the hyperthermophilic (or extremely thermophilic) microorganisms belong to a new evolutionary class called Archaea (Woese, C. R., Kandler, O. and Wheelis, M. L. "Towards a Natural System of Organisms: Proposal for the Domains Archaea, Bacteria, and Eucarya," *Proc. Natl. Acad. Sci. USA* 87:4576–4579, 1990). The Archaea are believed to have originated over a billion years ago during the epoch when the Earth was cooling. Consequently their evolutionary development was set in motion within the environment of hot springs and deep sea hydrothermal vents. One member of this new group is *Pyrococcus furiosus* which grows optimally at 100° C.–110° C. (Fiala, G. and Stetter, K. O. "*Pyrococcus furiosus* s. Nev. Represents a Novel Genus of Marine Heterotrophic Archaebacteria Growing Optimally at 100° C.," *Arch. Microbiol.* 145:56–61, 1986). *Pyrococcus furiosus* is an obligate heterotroph that can be grown on polymeric substrates including protein and starch at temperatures of up to about 103° C. Preparations containing proteolytic enzymes prepared from *Pyrococcus furiosus* have been previously described in U.S. Pat. Nos. 5,242,817 and 5,391,489. These patents do not describe the enzymes identified by the current applicant. Other publications describing proteases from *P. furiosus* also do not describe the current enzymes. See, for example, Blumentals, Ilse I., Robinson, Anne S., and Kelly, Robert M., "Characterization of Sodium Dodecyl Sulfate-Resistant Proteolytic Activity in the Hyperthermophilic Archaebacterium *Pyrococcus furiosus.*" *Applied and Environmental Microbiology*, 56,7:1992–1998, (1990); Eggen, Rik, Geerling, Ans, Watts, Jennifer and de Vos, Willem M., "Characterization of pyrolysin, a hyperthermoactive serine protease from the archaebacterium *Pyrococcus furiosus.*" *FEMS Microbiology Letters*, 71:17–20 (1990); Voorhorst, Wilfried G. B., Eggen, Rik I. L., Geerling, Ans C. M., Platteeuw, Christ, Siezen, Roland J., de Vos, Willem M., "Isolation and Characterization of the Hyperthermostable Serine Protease, Pyrolysin, and Its Gene from the Hyperthermophilic Archaeon *Pyrococcus furiosus.*" *Journal of Biological Chemistry*, 271,34: 20426–20431 (1996).

The use of proteolytic enzymes for selective peptide bond synthesis has been previously investigated. The majority of studies so far on protease-mediated peptide synthesis have utilized what has been called "semi-synthesis". In these reactions, the acyl donor is a substrate for the enzyme (amide or ester). The substrate is utilized to acylate the enzyme (e.g., a serine or thiol protease) followed by deacylation by C-terminally blocked amino acid or peptide. (See Nakatsuka, T., Sasaki, T., and Kaiser E. T. "Peptide Segment Coupling Catalyzed by the Semisynthetic Enzyme Thiolsubtilisin." *J Am. Chem Soc.* 109:3808–3810, 1987; Abrahmsen, L., Tom, J., Bumier, J., Butsher, K. A., Kossiakoff, A., and Wells, J. A., "Engineering Subtilisin and its Substrates for Efficient Ligation of Peptide Bonds in Aqueous Solution." *Biochemistry* 30:4151–4159, 1991; Christenen, U., Drohse, H. B., and Molgaard, L., "Mechanism of Carboxypeptidase-Y-catalyzed Peptide. Semisynthesis" *Eur J. Biochem.*, 210:467–473, 1992.

The ability to synthesize peptides and ligate polypeptides in aqueous solution under controlled conditions would be highly advantageous. Current protein synthesis methodologies result in much reactant and solvent toxic waste, which must be disposed of.

BRIEF SUMMARY OF THE INVENTION

In one embodiment, the subject invention provides new proteases useful in the efficient hydrolysis of peptide bonds. Advantageously, these proteases have been found to be active both as endo- and exopeptidases. Therefore, these enzymes can be used in a wide variety of applications where it is needed to remove amino acids from the end of a polypeptide, or cleave the polypeptide at an internal site.

In a preferred embodiment, the proteases of the subject invention have a molecular weight of about 81 kD and are serine proteases which retain enzymatic activity at about 100° C. In a specific embodiment a protease of the subject invention can be obtained from the extreme thermophile *Pyrococcus furiosus*.

A further embodiment of the subject invention concerns nucleotide sequences which encode the proteases of the subject invention. These sequences, which can be obtained from, for example, *P. furiosus*, can be used to express the enzymes of the subject invention. These sequences, and portions thereof, are also useful as nucleotide probes to identify and characterize other related sequences. The nucleotide sequences of the subject invention can also be used as primers in PCR procedures used to obtain or characterize additional nucleotide sequences of the subject invention.

A further aspect of the subject invention concerns antibodies to the proteases described herein. These antibodies can be used to identify and/or characterize the proteases of the subject invention.

A further aspect of the subject invention pertains to the use of the proteases described herein in polypeptide synthesis procedures. These enzymes can be used to facilitate highly specific and efficient peptide synthesis. The enzymes of the subject invention can be used to ligate two or more peptides (reversal of endopeptidase activity), or successively add single amino acids to a peptide chain (reversal of carboxypeptidase activity). The enzymes of the subject invention can be used to synthesize peptide bonds at high temperatures with high yields. The synthesis of peptide bonds occurs, according to the subject invention, at equilibrium. The enzyme catalyzed peptide syntheses according to the subject invention are stereospecific, require little if any side chain protection and are devoid of racemization problems. Also, the ability to carry out these reactions in an aqueous solution is advantageous compared to current peptide synthesis procedures which result in the production of substantial quantities of solvent toxic waste.

A further aspect of the subject invention concerns methods for identifying thermostable proteases. These methods involve the identification of the formation of protein or peptide synthesis products produced by the ligation of substrates when a composition containing these known substrates is heated. The formation of polypeptides from the known substrates is indicative of the thermostable proteases present in the mixture.

DETAILED DISCLOSURE OF THE INVENTION

In one embodiment, the subject invention pertains to novel serine proteases which can be obtained from extremely thermophilic microorganisms. The enzymes of the subject invention are catalytically active at temperatures above 60° C. and, therefore, are useful in a variety of industrial processes.

Specifically exemplified herein is a novel serine protease which can be obtained from the extreme thermophile *Pyrococcus furiosus*. This enzyme has an apparent molecular weight of about 81 kDa as determined by SDS gel electrophoresis. Those skilled in the art will recognize that the apparent molecular weight of a protein as determined by gel electrophoresis will sometimes differ from the true molecular weight. Therefore, reference herein to the 81 kDa enzyme of the subject invention is understood to refer to proteins which migrate on a gel, as described herein, in a manner which is consistent with a protein of approximately that size, even if the true molecular weight is somewhat different.

The serine protease specifically exemplified herein is a carboxypeptidase enzyme. Thus, it belongs to the class of enzymes known as serine carboxypeptidases. The exemplified enzyme can act as an amidase, anilidase, and esterase. The enzyme recognizes both arginine and aromatic residues such as phenylalanine in the P1 position (nomenclature of Schechter and Berger)(Schechter, I., and Berger, A. "On the Size of the Active Site in Proteases. I. Papain." *Biochem. Biophys. Res. Commun.* 27:157–162, 1967). The enzyme is also an endopeptidase since it yields prophe+argpNA from PPANA (D-pro-phe-arg-pNA).

Certain of the properties of the serine protease specifically exemplified herein are very unique: 1) the enzyme is both an endopeptidase as well as a carboxypeptidase, 2) the enzyme displays intense product inhibition toward several synthetic peptide substrates, and 3) it is able to catalyze high-yield peptide synthesis.

The broad proteolytic activity of the enzymes of the subject invention as well as their thermal stability make these enzymes useful in a variety of protease applications. The high temperature proteolysis carried out using the enzymes of the subject invention is useful for many industrial applications including the food processing industry and waste removal.

The enzymes of the subject invention can also be used in peptide and protein synthesis. For this use, peptides (or polypeptides) can be efficiently joined in the presence of the enzymes of the subject invention by increasing the temperature of the reaction mixture until the thermodynamics favor the formation of peptide bonds and, thus, the synthesis of a longer polypeptide from peptide fragments. This use of the enzymes of the subject invention is made possible by the enzymes' retention of enzymatic activity at elevated temperatures.

Thus, in addition to their utility as proteases, the enzymes of the subject invention are capable of synthesizing peptide bonds with high yields. The utilization of these enzymes in protein synthesis has many advantages over current protein synthesis methods, which are based on semi-synthesis. One of the major practical problems associated with "semi-synthesis" is that it must be kinetically monitored, or controlled. That is, the synthetic reaction must be terminated at or near the time when synthetic yield is at a maximum. Otherwise, proteolysis of the synthetic product will supervene and it will be driven thermodynamically to essentially complete hydrolysis. Equilibrium peptide synthesis according to the subject invention does not suffer this disadvantage. Also, use of these enzymes in protein synthesis is particularly advantageous because stereospecificity is preserved. Furthermore, group protection and toxic solvents are unnecessary when polypeptide synthesis is carried out according to the subject invention. Unlike previously known procedures, the peptide synthesis carried out according to the subject invention can be done without the use of harmful organic solvents.

The subject invention further provides methods for identifying thermostable enzymes. In one embodiment crude cellular preparations (or other compositions which may contain a thermostable enzyme) can be assayed for the presence of thermostable enzymes. In this embodiment, peptide and/or polypeptide substrates can be added to the crude preparation. The composition can then be heated and analyzed for the presence of ligated peptides or polypeptides. In this embodiment, thermostable enzymes will catalyze the synthesis of polypeptides from the peptide or polypeptide substrates. Thus, the presence of thermostable enzymes can be identified by the formation of ligated polypeptides after heat treatment. The enzyme(s) responsible for the activity can then be identified through sequential isolation steps which remove inactive compounds and result in the isolation of the thermostable enzymes. The enzymes can then be purified and characterized according to standard procedures. The subject invention includes the enzymes obtained according to this assay procedure.

The new proteins provided here are defined according to several parameters. One critical characteristic of the proteins described herein is thermostable enzymatic activity. In a specific embodiment, these proteins are serine proteases. The enzymes and genes of the subject invention can be further defined by their amino acid and nucleotide sequences. The sequences of the molecules can be defined in terms of homology to certain exemplified sequences as well as in terms of the ability to hybridize with certain exemplified sequences. The enzymes provided herein can also be identified based on their immunoreactivity with certain antibodies.

The polynucleotide sequences and enzymes useful according to the subject invention include not only the full length sequences disclosed herein but also fragments of these sequences, as well as variants, mutants, and fusion proteins which retain the characteristic enzymatic activity of the proteins specifically exemplified herein. As used herein, the terms "variants" or "variations" of genes refer to nucleotide sequences which encode the same enzyme or which encode equivalent enzymes having proteolytic activity. As used herein, the term "equivalent enzymes" refers to enzymes having the same or essentially the same biological activity as the exemplified enzymes, albeit with different specificity.

It would be apparent to a person skilled in this art that genes encoding active enzymes can be identified and obtained through several means. The gene encoding the specific enzyme exemplified herein may be obtained from the specific isolate described herein. This gene, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these enzymes.

Equivalent enzymes and/or genes encoding these equivalent enzymes can be derived from extreme thermophile isolates and/or DNA libraries using the teachings provided herein. There are a number of methods for obtaining the enzymes of the instant invention. For example, antibodies to the specific enzyme disclosed and claimed herein can be used to identify and isolate other such enzymes from a mixture of proteins. Specifically, antibodies may be raised to the portions of the enzyme which are most distinct from other enzymes. These antibodies can then be used to specifically identify equivalent enzymes with the characteristic activity by immunoprecipitation, enzyme linked immunosorbent assay (ELISA), or western blotting. Antibodies to the enzyme disclosed herein, or to equivalent enzymes, or fragments-of these enzymes, can readily be prepared using standard procedures in this art. The genes which encode these enzymes can then be obtained from the host cell.

The subject invention concerns not only the polynucleotide sequences which encode these enzymes but also the use of these polynucleotide sequences to produce recombinant hosts which express the enzymes. The enzyme-encoding genes of the subject invention can be introduced into a wide variety of microbial or plant hosts. Expression of the gene results, directly or indirectly, in the intracellular production and maintenance of the enzyme.

Fragments and equivalents which retain the enzymatic activity of the exemplified proteins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, proteins. These variant DNA sequences are within the scope of the subject invention. As used herein, reference to "essentially the same" sequence refers to sequences which have amino acid substitutions, deletions, additions, or insertions which do not materially affect enzymatic activity. Fragments retaining enzymatic activity are also included in this definition.

A further method for identifying the proteins and genes of the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) *DNA Probes*, Stockton Press, New York, N.Y., pp. 169–170.

As used herein "stringent" conditions for hybridization refers to conditions which are able to distinguish genes encoding heat stable serine proteases from unrelated genes. Specifically, hybridization of immobilized DNA on Southern blots with 32P-labeled gene-specific probes can be performed by standard methods (Maniatis et al.). For double-stranded DNA gene probes, hybridization can be carried out overnight at 20–25° C. below the melting temperature (Tm) of the DNA hybrid in 6×SSPE, 5× Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266–285).

Tm=81.5° C.+16.6 Log [Na+]+0.41(% G+C)−0.61(% formamide)−600/length of duplex in base pairs.

Washes are typically carried out as follows:
(1) Twice at room temperature for 15 minutes in 1×SSPE, 0.1% SDS (low stringency wash).
(2) Once at Tm−20° C. for 15 minutes in 0.2×SSPE, 0.1% SDS (moderate stringency wash).

For oligonucleotide probes, hybridization can be carried out overnight at 10–20° C. below the melting temperature (Tm) of the hybrid in 6×SSPE, 5× Denhardt's solution, 0.1% SDS, 0.1 mg/ml denatured DNA. Tm for oligonucleotide probes can be determined by the following formula:

Tm(° C.)=2(number T/A base pairs)+4(number G/C base pairs)

(Suggs, S. V., T. Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683–693).

Washes can be typically carried out as follows:
(1) Twice at room temperature for 15 minutes 1×SSPE, 0.1% SDS (low stringency wash).
(2) Once at the hybridization temperature for 15 minutes in 1×SSPE, 0.1% SDS (moderate stringency wash).

With the teachings provided herein, one skilled in the art could readily produce and use the various enzymes and polynucleotide sequences of the novel enzymes described herein.

Detection of the probe provides a means for determining in a known manner whether hybridization has occurred. Such a probe analysis provides a rapid method for identifying enzyme-encoding genes of the subject invention. The nucleotide segments which are used as probes according to the invention can be synthesized using a DNA synthesizer and standard procedures. These nucleotide sequences can also be used as PCR primers to amplify genes of the subject invention.

Certain enzymes of the subject invention have been specifically exemplified herein. Since these enzymes are merely exemplary of the enzymes of the subject invention, it should be readily apparent that the subject invention comprises variant or equivalent enzymes (and nucleotide sequences coding for equivalent enzymes) having the same or similar enzymatic activity of the exemplified serine protease. Equivalent enzymes will have amino acid homology with the exemplified enzyme. This amino acid homology will typically be greater than 60%, preferably be greater than 75%, more preferably greater than 80%, more preferably greater than 90%, and can be greater than 95%. The amino acid homology will be highest in critical regions of the enzyme which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: nonpolar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the enzyme.

Following are examples which illustrate procedures for practicing the invention. These examples should not be construed as limiting. All percentages are by weight and all solvent mixture proportions are by volume unless otherwise noted.

EXAMPLE 1

Isolation of a Serine Protease of the Subject Invention

*Pyrococcus furiosus* cells were obtained from Professor C. B. Anfinsen's laboratory at Johns Hopkins. These cells can also be obtained from Dr. Michael W. W. Adams at the University of Georgia. Natural Sources of these cells have been described in the literature. See, for example, references cited in the Background of the invention. Cells are centrifuged and 100 g (wet weight) is suspended in water and sonicated. Cell debris is removed by centrifugation and the resulting supernatant solution is dialyzed against 0.05 M tris-HCl, pH 7.5.

Four chromatographic steps are utilized to yield an electrophoretically and ultracentrifugally homogeneous macromolecule. The entire purification scheme utilizes FPLC (Pharmacia) and all chromatographic fractions are screened for enzyme activity (at 25° C.) using N-benzoyl-L-arginine-p-nitroanilide (BAPNA) as substrate.

The chromatographic steps are as follows:
a. The crude sonicate is applied to Mono Q 10/10 equilibrated with 0.05 M tris-HCl, pH 7.5 linear 184 ml gradient to 0.4 M KCl, 3 ml/min. Active fractions are pooled and dialyzed vs. 0.05 M sodium acetate, pH 4.5.
b. Mono S 10/10, 0.05 M sodium acetate, pH 4.5, linear 368 ml gradient to 1.0 M NaCl at 3 ml/min.
c. Mono Q 5/5 0.05 M histidine, pH 5.5, linear gradient (23 ml) to 0.4 M KCl at a flow rate of 1 ml/min.
d. The pooled fractions from (c) are concentrated by membrane filtration and applied to a 2.6×60 cm column of Superdex-200 equilibrated with 0.1 M tris-HCl, 0.1 NaCl, pH 7.5.

Throughout the above ion-exchange steps (a–c), the chromatographic profiles reveal 2 prominent protein peaks that display BAPNA anilidase activity, together with other BAPNA-positive peaks in much lower amounts that are successively eliminated with each column step. The last step (gel filtration) yields 2 well-separated protein fractions that represent approximately 80% and 15% of the anilidase activity present in the original cell sonicate. The most abundant of these 2 proteins is the one used for all of the studies described below. It emerges from the Superdex-200 column with an apparent molecular weight of about 110,000 as judged from its partition coefficient determined with standard gel filtration molecular weight marker proteins. Polyacrylamide gel electrophoresis (SDS-PAGE) yields a single sharp band under reducing conditions. The estimated molecular weight of this band is approximately 81,000. The yield is approximately 1 mg of pure protein from 100 g wet cells.

EXAMPLE 2

Extinction Coefficient, Apparent Partial Specific Volume, and Molecular Weight of Serine Protease of the Subject Invention The protein was hydrolyzed (constant boiling HCl) for 18,22,24 and 26 hours. From absorbance measurements (280 nm) and the methods of Edelhoch (Edelhoch, H. "Spectroscopic Determination of Tryptophan and Tyrosine in Proteins." *Biochemistry* 6:1948–1954, 1967), the extinction coefficient was calculated to be 1.31 ml mg$^{-1}$cm$^{-1}$.

Sedimentation equilibrium measurements utilized a Beckman Model E ultracentrifuge equipped with a split-beam scanner and multiplexer for visualization of two centrifuge cells during the same run. The high speed method of Yphantis (Yphantis, D. A. "equilibrium Ultracentrifugation of Dilute Solutions," *Biochemistry* 3:294–303, 1964) was employed together with the methods of Edelstein and Schachman for simultaneous measurement of the partial specific volume (Edelstein, S. J. and Schachman, H. K. "The Simultaneous Determination of Partial Specific Volumes and Molecular Weights with Microgram Quantities." *J Biol. Chem.* 242:306–311, 1967). One cell contained protein dialyzed thoroughly against 0.1 M tris-HCl, pH 7.5, in H$_2$O and the second cell contained the enzyme in the same buffer with 99% D$_2$O as solvent (densities of the buffer solutions were measured pycnometrically). Centrifugation (20,000 RPM, 23.5EC) yielded a molecular weight of approximately 81,500 and an apparent partial specific volume (Casassa, E. F. and Eisenberg, H. "Thermodynamic Analysis of Multicomponent Solutions." *Adv. Prot. Chem.* 19:287–393,1964) of 0.789 ml/g. This is a surprisingly high value for the specific volume of a protein and it implies a larger than expected Stokes radius, which may explain why the protein emerges earlier upon gel filtration than would be anticipated for a protein of molecular weight of 81,500. Plots of ln c vs r$^2$ were strictly linear—a feature that indicates size homogeneity. The close similarity of the molecular weight to that obtained by SDS-PAGE indicates that the protein has a single polypeptide chain structure.

EXAMPLE 3

Stability of Enzymic Activity at High Temperature

For all kinetic experiments at high temperatures, sodium phosphate (0.025 M) was used as a buffer. The temperature coefficient of this buffer is so small that slight changes in pH with temperature do not significantly affect the kinetic data.

To assess stability of the enzyme at high temperature, a solution of the protein in the above buffer, pH 7.0, was incubated at 82.0+/−0.05° C. Aliquots were removed at hourly intervals up to 8 hr, and initial velocities were measured (BAPNA as substrate, Varian 2290 recording spectrophotometer) at 25.0°+/−0.05° C. (Erlanger, B. F., Kokowski, N. and Cohen, W. "The Preparation and Properties of Two New Chromogenic Substrates of Trypsin." *Arch. Biochem. Biophys.* 95:271–278, 1961). No decrease in enzyme activity was observed over this time period.

EXAMPLE 4

Activation Enthalpy and Entropy as a Function of Temperature

To explore the basis for the extremely large increases in enzyme activity with temperature, initial velocity (v$_o$) measurements were made at 6 different substrate concentrations in order to determine k$_{cat}$ and K$_m$ at a series of temperatures in the range of 25.0 to 83.5° C. Temperature was controlled to within +/−0.5° C. with a large water bath and jacketed cuvettes. Two substrates were used for these experiments—BAPNA and D-pro-phe-arg-pNA(PPANA). From these data, Arrhenius plots were constructed (ln v$_o$ vs 1/T° K).

Within the temperature range accessible to mesophilic enzymes, such plots are linear. The plot with BAPNA as substrate exhibits considerable continuous curvature. The data was fitted to a second degree polynomial and the slopes determined as a function of temperature to compute Arrhenius activation energies. These values were used to compute activation enthalpy ($\Delta H^*$) and entropy ($\Delta S^*$) as a function of temperature (Eyring, H. (1963) *Modern Chemical Kinetics*, Rheinhold, New York). Table 2 summarizes these values for BAPNA and D-pro-phe-arg-pNA at 25.0° and 80.0° C.

TABLE 2

$\Delta H^*$ and $\Delta S^*$ as a Function of Temperature

| Substrate | T° C. | $\Delta H^*$ (kcal/mole) | $\Delta S^*$ (e.u) |
|---|---|---|---|
| BAPNA | 25.0 | 17.2 | 2.2 |
| BAPNA | 80.0 | 3.1 | −41.7 |
| PPANA | 25.0 | 26.1 | 23.8 |
| PPANA | 80.0 | 15.4 | −9.0 |

The data and Table 2 show that the activation energy barrier falls markedly, in a continuous fashion, as temperature increases. Furthermore, the fact that the Arrhenius plots are smoothly monotonic indicates that no sharp, discontinuous structural transition (e.g., from less active to more active enzyme) occurs. The process appears to be continuous from 25–80° C. The entropies become negative at higher temperatures.

EXAMPLE 5

Active Site Inhibitor Studies

To assign the class of protease to which the *P. furiosus* protease belongs, several reagents were used to identify catalytically important residues. BAPNA was the substrate for all of the following results:
  a. Incubation of the enzyme with 10$^{-3}$ M EDTA for 24 hr had no effect upon enzyme activity.
  b. One of the active-site inhibitors of mesophilic serine proteases is phe-pro-argCH$_2$Cl. This reagent reacts rapidly and specifically with the active site histidine residue of the active site triad: ser-his-asp (Shaw, E. "Site-Specific Reagents for Chymotrypsin and Trypsin." *Math. Ensemble.* 11:677–686, 1967). Treatment of the *P. furiosus* enzyme with this inhibitor ($1.98 \times 10^{-6}$ M) together with kinetic measurements of BAPNA enzymic activity (BAPNA=$3.8 \times 10^{-4}$ M) vs time at 25.0° C. yielded a pseudo first order inactivation rate constant=0.022 sec$^{-1}$.

c. Treatment of the enzyme with PMSF (phenyl-methyl-sulfonyl fluoride) $8 \times 10^3$ molar excess over enzyme, resulted in complete inhibition of enzyme activity with BAPNA as the assay substrate at 25.0° C.

d. The following reagents had no affect whatsoever upon the activity of this enzyme at 25.0° C.: i) 0.025 M sodium phosphate, pH 7.0; ii) iodoacetamide: 100-fold molar excess: enzyme; iii) bisdithiodintrobenzene (Ellman's reagent).

Taken together, the above results confirm that the protease active site does indeed contain histidine and serine, and that it is a serine protease, not a thiol enzyme.

EXAMPLE 6

Kinetic Studies and Substrate Specificity

The hydrolysis kinetics of various synthetic peptide and ester protease substrates were studied. Two different methods have been used to analyze the kinetic properties of the enzyme. The first utilized initial velocity data at several substrate concentrations with analysis by plotting s/v vs s (Hanes plot). This method was always used when it was possible that the protease could cleave at more than one site (e.g., PPANA). The second method utilizes all data of the progress curve of the reaction. Progess curves were analyzed in two ways:

a. v vs s.

Instantaneous point by point derivatives were calculated from the absorbance vs time data by fitting 10 points spaced 1 second apart by least squares to a second degree polynomial. Derivatives were computed analytically and were used to construct plots of v vs s, which were then analyzed by non-linear regression to obtain $K_m$, $k_{cat}$ and any product inhibition constant ($K_i$) if it exists. The advantages of this method are that it does not require a precise value of the initial substrate concentration, (Koerber, S. C. and Fink, A. L. "The Analysis of Enzyme Progress Curves by Numerical Differentiation, Including Competitive Product Inhibition and Enzyme Reactivation." *Anal. Biochem.* 165:75–87, 1987), and it can readily be used to correct for non-enzymic substrate hydrolysis at high temperatures. For all measurements at elevated temperature, the first-order rate constants for non-enzymic hydrolysis were determined for all substrates. The analytic method described here was used both for reactions at 25.0° C. and 80.0° C.

b. Integrated Rate Equation Analyses: t vs Absorbance.

For these analyses, the integrated Michaelis-Menten equation was used, but not in linearized form, for reasons relating to product inhibition. Plots of time (now the dependent variable) vs absorbance were constructed from the raw data and analyzed by non-linear regression. In these analyses, the initial substrate concentration is taken as a parameter to be fit in the non-linear regression—a procedure that has been shown to provide more accurate values of the kinetic parameters (Newman, P. F. J., Atkins, G. L. and Nimmo, I. A., "The Effect of Systematic Error on the Accuracy of Michaelis Constants and Maximum Velocities Estimated by Using the Integrated Michaelis-Menten Equation." *Biochem. J* 143:779–781, 1974). This method was used for analyses at 25.0° C. only.

c. Computer Methods.

Subroutines for the above analyses were written to analyze the kinetic data for: product competitive inhibition, non-competitive inhibition, 2-product inhibition, and simple Michaelis-Menten kinetics. An HP 9000 series work station was used for this purpose, using HP BASIC.

The substrates studied by the above methods are listed here and all data are summarized in Table 3. All kinetic studies utilized a Cary 3E double beam spectrophotometer and absorbance vs time data were collected by computer at 1 second intervals. In cases where a peptide substrate could potentially be cleaved at more than one site, thin-layer chromatography was used to establish the products formed (silica gel; butanol: acetone: $NH_4OH$:water—37:37:19:7).

1. BAPNA (Benzoyl-arginine-p-nitroanilide)

The slope of the Hanes plot for BAPNA at 25.0° is negative. This can only mean that the reaction is product inhibited and that $K_i < K_m$ for this substrate.

Table 3 shows that $K_i$ is 10 times less than $K_m$. This result reflects very tight binding of one of the two products of BAPNA hydrolysis to the protein. To determine the inhibition constants of the products, initial rate measurements of BAPNA were conducted with varying concentrations of the two products—benzoyl-arg and p-nitroaniline. p-nitroaniline displayed no detectable inhibition at concentrations as high as $5 \times 10^{-4}$ M, whereas benzoyl-L-arginine strongly inhibited with $K_i = 6.50 \times 10^{-5}$ M. This number is close to that ($7.08 \times 10^{-5}$ M) obtained from total progress curve analyses. This close agreement of the $K_i$ values determined by totally different analytic methods also lends credence to results from the total progress curve data that have been analyzed by non-linear regression methods. Such strong product inhibition is exceptional.

A second unusual feature concerns the $k_{cat}$ value for BAPNA at 25.0° C. (see Table 3). The $k_{cat}$ value for BAPNA as substrate is greater than that for trypsin under the same conditions ($k_{cat} = 2.7$ sec$^{-1}$). The value of $k_{cat}$ is 65 times greater at 80° C. than at 25° C.

2. PPANA (D-pro-phe-arg-pNA)

Continuous progress curve analyses of this substrate indicated that it can be cleaved at more than one bond. The substrate was completely depleted before the expected amount of pNA had been liberated. Therefore, initial rates were used to determine the values given in Table 3. It will be seen that kcat is 120 times greater at 80° C. than at 25° C. TLC demonstrated that the protease:

a. produces pro-phe-arg+pNA
b. cleaves pro-phe-arg 6 pro-phe+arg
c. cleaves substrate 6 pro-phe+arg-pNA
d. does not hydrolyze arg-pNA at all, even at 80° C.

The above results indicate that this protease has endopeptidase as well as carboxypeptidase activity.

3. BTEE (benzoyl-tyrosine ethyl ester).

The protease cleaves this substrate with a large $k_{cat}$ at 25° C. Thus, the protease is also an esterase.

4. FAGLA (furyl-acryloyl-glycyl-leucine amide)

This commonly used thermolysin substrate shows intense product inhibition. TLC demonstrates that the protease only deamidates the substrate. It does not split the gly-leu bond. $K_i < K_m$.

5. FAPP (furyl-acryloyl-phe-phe)

Cleavage occurs to liberate only FAP plus phe (TLC), and product inhibition is not observed. Only a simple Michaelis- Menten mechanism will fit the experimental data. This is the second example of carboxypeptidase-like activity.

6. FAAPA (filryl-acryloyl-ala-phe-amide)

Like FAGLA, the enzyme deamidates this substrate with $K_i<K_m$. TLC reveals only FAAP as a product. No cleavage occurs at the ala-phe bond.

7. ZPA (carbobenzoxy-phe-ala)

Ala is liberated in carboxypeptidase fashion, again with $K_i<K_m$.

8. FAPGG (furyl-acryloyl-phe-gly-gly)

The enzyme only hydrolyzes the phe-gly bond with liberation of FAP+gly-gly. No product inhibition is observed. This is another example of the endopeptidase activity of the enzyme.

9. Finally, two reagents remain unaltered by the enzyme—HA (hippuryl-arginine) and ZGP (carbobenzoxy-gly-phe).

TABLE 3

| Substrate | T° C. | $k_{cat}(sec^{-1})$ | $K_m(M)$ | $K_i(M)$ |
|---|---|---|---|---|
| BAPNA | 25.0 | 6.27 | $7.37 \times 10^{-4}$ | $7.08 \times 10^{-5}$ |
| BAPNA | 80.0 | 406 | $7.78 \times 10^{-4}$ | $2.20 \times 10^{-4}$ |
| PPANA | 25.0 | .045 | $4.77 \times 10^{-4}$ | N.D. |
| PPANA | 80.0 | 5.44 | $4.99 \times 10^{-4}$ | N.D. |
| BTEE | 25.0 | 27.4 | $6.57 \times 10^{-4}$ | $5.6 \times 10^{-3}$ |
| FAGLA | 25.0 | 0.67 | $6.08 \times 10^{-6}$ | $2.79 \times 10^{-6}$ |
| FAPP | 25.0 | 4.58 | $3.75 \times 10^{-4}$ | None |
| FAAPA | 25.0 | 7.31 | $3.86 \times 10^{-5}$ | $1.57 \times 10^{-5}$ |
| HA | 25.0 | — | — | — |
| ZPA | 25.0 | 3.65 | $5.55 \times 10^{-4}$ | $1.34 \times 10^{-4}$ |
| ZGP | 25.0 | — | — | — |
| FAPGG | 25.0 | 10.64 | $4.15 \times 10^{-4}$ | — |

All of the above are mean values from at least 4 separate experiments. Except for PPANA, values are means of v vs s and integrated rate equation analyses. PPANA values were obtained from initial velocity measurements, analyzed by the Hanes equation. Solvent: 0.025 M Na Phosphate, pH 7.0. 2000–5000 data points were used for the above analyses (except for PPANA). N.D. means not determined.

All peptide substrates listed in Table 3 yield product inhibition constants ($K_i$) that are approximately 3–10 lower than $K_m$ values.

EXAMPLE 7

Substrate Specificity

Treatment of the insulin B-chain with the serine protease of the subject invention (80° C., phosphate buffer, pH 7.0) for 1 hour yields 5 ninhydrin-positive components by TLC. No non-enzyme hydrolysis of substrate was detected after this time period. One of the new components is alanine which the carboxy terminus of the B-chain. None of the others is a free amino acid. These studies with insulin provide further evidence that the enzyme is an endopeptidase.

EXAMPLE 8

Peptide Synthesis

Benzoyl-arginine ethyl ester was selected as an acyl donor because of the very low product inhibition constants observed for benzoyl-arginine ($K_i=7.08\times10^{-5}$ M, Table 3). Leucine-amide was chosen as nucleophile. Reaction solutions 0.025 M Na-phosphate, pH 7.0, at 25.0° C. contained $6.9\times10^{-3}$ M BAEE, 0.091 M leucine-amide and 0.015 mg/ml protease. Aliquots were removed over time and analyzed by TLC as described earlier. After 45 min at 25° C., the yield of benzoyl-arginine-leucine amide was approximately 50% from TLC and HPLC analyses. This represents considerable synthesis over a relatively short time period and it occurs at 25° C.

Two different peptides have been synthesized at pH 5.5 and 85° C. These peptides are as follows:

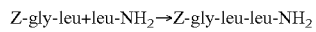

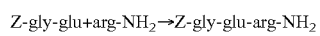

Reactions were terminated after 3 hours at 85° C. and reaction solutions were analyzed by FPLC. The synthetic products were verified by mass spectroscopy. For both reactions, the concentration of the amine nucleophile was 0.9M. The protease concentration was 10 µg/ml.

Table 4 summarizes the results. Yield is defined as the ratio of product concentration to the initial concentration of the carboxyl reactant (in percent). Theoretical yield was calculated from equations 1, 2 and 3 together with $pK_1=3.81$ (ZGL) and 4.47 (ZGE); $pK_2=7.93$ (leu-$NH_2$) and 7.51 (arg-$NH_2$).

TABLE 4

| Reaction | [Carboxyl] | Yield | Yield (theory) | $\Delta G°_{net}$ | $K_{net} (M^{-1})$ |
|---|---|---|---|---|---|
| ZGL + leu – $NH_2$ | 0.01 M | 48% | 55% | −0.021 | 1.03 |
| ZGE + arg – $NH_2$ | 0.048 M | 60% | 68% | −0.380 | 1.72 |

*$\Delta G°_{net}$ (kcal/mole) and $K_{net}$ are the experimental values.

The yields for peptide synthesis presented in Table 4 are far greater than any previously reported values under equilibrium conditions. Moreover, the above reactions were carried out in the absence of organic co-solvents and in the absence of product precipitation to drive the reactions. As shown in Table 4, the actual yields of synthesis product are remarkably close to predicted values.

EXAMPLE 9

Peptide Sequencing

The amino acid sequence of the first 20 amino-terminal residue was found to be:

```
SSIEWNEKTFAKFAYLSDPR.      (SEQ. ID NO. 1)
```

No identical matches to this sequence could be found in the data banks. An analysis of the initial eight amino acids strongly favors a single peptide chain, in agreement with electrophoretic and ultracentrifugal analyses. To obtain internal amino acid residue sequences, the protein can be digested by chymotrypsin or trypsin attached to beaded agarose. After pelleting to remove the beads, the fragmented protein can be subjected to SDS-PAGE and stained. The digest lane can be transferred to PVDF membrane. Well-separated bands are then subjected to sequencing.

EXAMPLE 10

Cloning and Sequencing of the Gene Encoding the Serine Protease from *Pyrococcus Furiosus*

The gene encoding the serine protease specifically exemplified herein can be cloned and sequenced by a person skilled in the art having the benefit of the instant disclosure. One cloning method involves screening a genomic library of *P. furiosus*. A *P. furiosus* genomic library is commercially available from Sybtrel Biotechnology. The average insert size is approximately 7 kilobase pairs indicating that approximately 8000 transformants must be screened in order to have a 99% chance of full coverage of the genome (Sambrook, J., Fritsch, E. F. and Maniatis, T. *Molecular Cloning, A Laboratory Manual*, 2nd edition. Cold Spring Harbor Laboratory Press, 1989). An oligonucleotide probe based on the partial protein sequence has been designed to identify for the serine protease gene by hybridization. This probe has the following sequence:

```
GA(AG)TGGAA(TC)GA(AG)AA(AG)AC.    (SEQ. ID NO. 2)
```

This oligonucleotide has only eight-fold redundancy providing a high probability of specific hybridization to the target gene DNA with minimal background.

The library can be transformed into *E. coli* strain DH5α by the $CaCl_2$ method (Sambrook, J., Fritsch, E. F. and Maniatis, T. *Molecular Cloning, A Laboratory Manual*, 2nd edition. Cold Spring Harbor Laboratory Press, 1989). The Sybtrel library was established in a pUC 19 vector system so transformants can be selected based on resistance to ampicillin, and spread to yield a density of approximately 500 colonies per LB-Ap plate. Colonies can be lifted onto nitrocellulose filter discs. The discs are washed with 10% SDS to lyse the cells and the DNA denatured under alkaline conditions (0.5 M NaOH, 1.5 M NaCl, 5 min). Following neutralization and a buffer wash, the filters are dried under vacuum at 80° C. for 1 hour. The probe oligonucleotide can be end labeled with $^{32}$p using T4 DNA kinase (New England Biolabs, Beverly, Mass.). The filters can be prehybridized using salmon sperm DNA as a blocking agent, and then hybridization can be at 45° C. overnight. The filters are then washed under progressively higher stringency by raising the wash temperature. Positive hybridization signals can be detected by autoradiography. Colonies corresponding to positive signals can be picked, restreaked and subjected to successive rounds of hybridization screening until pure cultures are obtained.

The size of *P. furiosus* DNA inserts in positive clones can be determined by EcoRI digestion and a preliminary restriction map developed. This facilitates generation of a series of nested deletions for DNA sequence analysis. DNA sequencing can be performed in an automated DNA facility using the vector specific universal primer. Alternatively as the sequence emerges, *P. furiosus* DNA specific primers can be generated to obtain sequence from areas which are too distant from the universal priming site or simply prove difficult to sequence (i.e., high GC content regions).

The following criteria can be used to establish that the cloned gene codes for the *P. furiosus* serine protease. First, the full length native protein obtained as described herein has a molecular weight of approximately 81,500 daltons suggesting an open reading frame of at least approximately 2000–2200 base pairs (taking into account some potential post-translational processing). The deduced primary sequence should match the partial amino acid sequence derived from the native protein.

It should be understood that the examples and embodiments described herein are for illustrative purposes only and that various modifications or changes in light thereof will be suggested to persons skilled in the art and are to be included within the spirit and purview of this application and the scope of the appended claims.

The invention claimed is:

1. A method for identifying thermostable proteases that catalyze the formation of peptide bonds comprising:

(a) contacting a solution to be assayed for the presence of a thermostable protease with known peptide or polypeptide substrates to form a mixture;

(b) heating said mixture to a temperature of about 60 degrees C. or higher; and (c) detecting the formation of a new peptide bond between said substrates;

wherein said method is performed in the absence of organic co-solvents, product precipitation and activated amino acids.

* * * * *

UNITED STATES PATENT AND TRADEMARK OFFICE
CERTIFICATE OF CORRECTION

PATENT NO.         : 7,192,730 B2                                          Page 1 of 1
APPLICATION NO. : 10/825921
DATED              : March 20, 2007
INVENTOR(S)        : David Michael Young It is certified that error appears in the above-identified patent and that said Letters Patent is hereby corrected as shown below:

Column 9,
Line 16, "ofthis band" should read --of this band--.

Column 9,
Line 55, "In c vs $r^2$" should read --ln c *vs* $r^2$--.

Signed and Sealed this

Third Day of July, 2007

JON W. DUDAS
*Director of the United States Patent and Trademark Office*

```
                         SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO: 1:

Ser Ser Ile Glu Trp Asn Glu Lys Thr Phe Ala Lys Phe Ala Tyr Leu
1               5                   10                  15

Ser Asp Pro Arg
            20

(2) INFORMATION FOR SEQ ID NO: 2:

(i) SEQUENCE CHARACTERISTICS:
          (A) LENGTH: 17 base pairs
          (B) TYPE: nucleic acid
          (C) STRANDEDNESS: single
          (D) TOPOLOGY: linear
```

-continued (ii) MOLECULE TYPE: DNA (genomic)

(xi) SEQUENCE DESCRIPTION: SEQ ID NO: 2:

GARTGGAAYG ARAARAC                                               17